(12) United States Patent
Chavan et al.

(10) Patent No.: US 6,350,881 B1
(45) Date of Patent: Feb. 26, 2002

(54) PROCESS FOR THE PREPARATION OF 5-METHOXY-4-(METHYLTHIOALKYL) 1,3-BIS(PHENYLMETHYL)-2-IMIDAZOLIDONE

(75) Inventors: Subhash Prataprao Chavan; Subhash Krishnaji Kamat; Beena Rai; Latha Sivadasan; Kamalam Balakrishnan; Ramalingam Sadyandi; Amar Gopal Chittiboyina; Vishnu Hari Deshpande, all of Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/724,501
(22) Filed: Nov. 28, 2000
(51) Int. Cl.$^7$ .............................................. C07D 233/30
(52) U.S. Cl. ...................... 548/319.1; 548/154
(58) Field of Search ........................................ 548/318.1

(56) References Cited

U.S. PATENT DOCUMENTS 5,250,699 A * 10/1993 Casutt et al. ............ 548/319.1

* cited by examiner

*Primary Examiner*—Laura L. Stockton
(74) *Attorney, Agent, or Firm*—Ladas & Perry

(57) ABSTRACT

This invention provides a process for the preparation of 5-methoxy-4-(methylthioalkyl)-1,3-bis(phenylmethyl)-2-imidazolidone having general formula (2a–d)

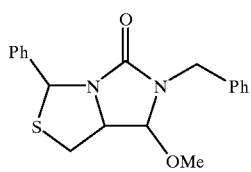

1

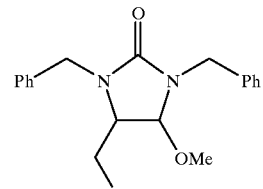

2 a: R = CH$_2$COCH$_2$CH$_2$CH$_2$COOMe
b: R = CH$_2$CH(OMe)$_2$
c: R = CH$_2$COOMe
d: R = H

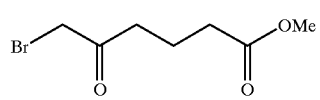

3a

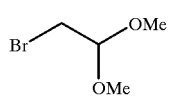

3b

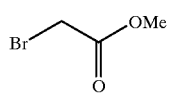

3c

[wherein R=—CH$_2$COCH$_2$CH$_2$CH$_2$COOMe (2*a*); —CH$_2$CH(OMe)$_2$(2*b*); —CH$_2$COOMe(2*c*); —H (2*d*)] which comprises reacting a reducing agent with 6-benzyl-7-methoxy-3-phenylperhydroimidazo[1,5-c][1.3]thiozol-5-one in the presence of an organic solvent for a period ranging from 0.5 to 2 hrs at a temperature ranging from −78° C. to 80° C., evaporating the solvent and reacting the residue with an alkylating reagent, optionally in the presence of a phase transfer catalyst and an inorganic base in an organic solvent for a period ranging from 10–12 hrs at room temperature, evaporating the solvent followed by purification to obtain the desired compound of general formula 2 *a–d*.

6 Claims, No Drawings

PROCESS FOR THE PREPARATION OF 5-METHOXY-4-(METHYLTHIOALKYL) 1,3-BIS(PHENYLMETHYL)-2-IMIDAZOLIDONE

FIELD OF THE INVENTION

The invention particularly relates to an improved process for the preparation of 5-methoxy-4-(methylthioalkyl)-1,3-bis(phenylmethyl)-2-imidazolidone of general formula 2, [wherein R=—CH$_2$COCH$_2$CH$_2$CH$_2$COOMe (2a); —CH$_2$CH(OMe)$_2$(2b); —CH$_2$COOMe(2c); —H (2d)] useful for the synthesis of D(+)biotin.

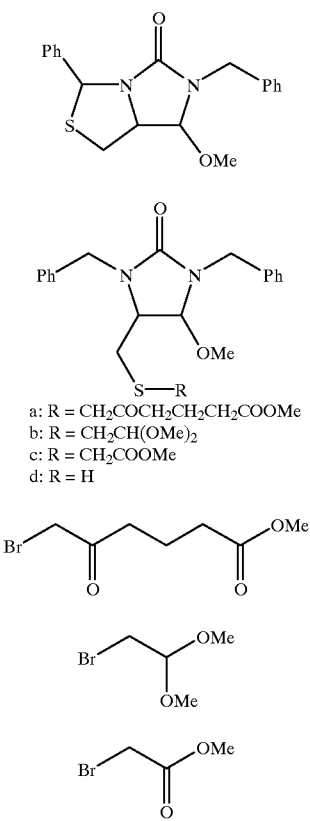

BACKGROUND OF THE INVENTION

Biotin (vitamin H) is one of the B-complex group of vitamins, has immense commercial importance in the area of animal health and nutrition. It is one of the biocatalyst of the reversible metabolic reactions of carbon dioxide transport in micro and macro organisms. It is used in the poultry feed for rapid growth of chicks and healthy hatching of eggs. Biotin-avidin complex finds a vital role in the area of biochemistry.

D(+)-Biotin prepared by the process of the present invention has the formula (4).

Formula 4

D(+)-biotin is prepared in the prior art from amino acids vis., cysteine, cystine and serine. These processes involving L-crystine as the precursor, incorporate intramolecular radical cyclization (E. J. Corey, M. M. Mehorotra, *Tet. Lett.*, 29, 57 1988) as the key step is construct the tetrahydrothiophene moiety of biotin.

Another prior art process involves intramolecular cycloaddition (3+2) of derivatives of L-cystine (E. G. Baggiolini, H. L. Lee, G. Pizzolato and M. R. Uskokovic, *J. Am. Chem. Soc.*, 104, 6460, 1982), and L-cysteine (H. L. Lee, G. Baggiolini and M. R. Uskokovic, *Tetrahedron* 43, 4887, 1987).

In another process starting from L-cysteine, a bicycle imidazolidine is the key intermediate leading to D(+)-biotin (E. Poetsch and M. Casutt, EP 242,686 1986 CA:108:112077k 1988; *Chimia* 41, 148, 1987). In a totally different and novel approach, L-cysteine was converted to its thiazolidine derivative which on treatment with bromine is converted stetreospecifically to a bicyclic intermediate as a single stereoisomer and eventually transformed to D(+)-biotin (P. N. Confalone, E. G. Baggioline, D. Lollar, and M. R. Uskokovic, *J. Am. Chem. Soc.*, 99, 7020 1977).

Process for stereospecific synthesis of D(+)-Biotin from sugars of suitable configuration are known. [From Mannose *Tet. Lett.*, 32, 2765 1975].

The use of L-cysteine in known from U.S. Pat. No. 4,000,972, U.S. Pat. No. 4,130,713, U.S. Pat. No. 4,337,345 and *J. Am. Chem. Soc.*, 99, 7020, 1977 avoids the handling of labile intermediate steps but involves 18 steps, in all with the separation of undesired isomer leading to unsatisfactory yields of optically active D(+)-Biotin.

In another process *J. Am. Chem. Soc.*, 105, 5946, 1983 and EP 0094776, substituted 3H, 5H-Imidazo[1,5-C]tetra hydro thiazole are described from which after racemate resolution, synthesis of optically active biotin is described.

In another process by Moolenaer, M. J.; Speckamp, W. N.; Hiemstra, H.; Poetsch, E.; Casutt, M. *Angew, Chem., Int. Ed. Engl.* 1995, 34, 2391 and DE 3,926,690 involves the intramolecular version of the condensation of a silyl enol ether with N-acyliminium intermediates to effect the ring closure of thio ether to the thiophane nucleus.

In yet another process by Poetsch, E.; Casutt, M., EP 242,686 1986; CA: 108: 112077K 1988; *Chimia* 41, 141–150, 1987 describes the formation of keto acid and further elaboration of acid to D(+)-Biotin. The main draw back of this method is use of hazardous 2 eq of diisobutylaluminium hydride (DIBAL-H), Potassium cyanide (KCN), Carbonyldiimidazole and involves reactions to be performed under anhydrous conditions.

In yet another prior art of biotin syntheses by Chavan, S. P.; Chittiboyina, A. G.; Kamat, S. K., Indian Patents NF135/98, 136/98 and Ravindranathan, T.; Chavan, S. P.; Tejwani, R. B. U.S. Pat. No. 5,274,107 (1993) describes the formation of substituted imidazolidines from L-cysteine and further elaboration of hydantoin to D(+)-biotin. This process also involves the use of expensive and hazardous chemicals vis., DIBAL-H, tertiary butyl dimethyl silyl chloride (TBDMSCI), trifluoromethane sulphonic acid (Triflic acid) etc., Hiterto known processes involve highly toxic and hazardous chemicals e.g., phosgene for the formation of imidazolidine. Moreover the intramolecular radical cyclization leads to both desired five member as well as undesired six member ring along with tin inclusion compounds as the undesired byproducts.

In another prior art process involving the intramolecular (3+2) cycloaddition reaction of nitrone, the precursor olefin is obtained as a mixture (9:1) of which the desired olefin has to be purified and separated by chromatography. Moreover, the chiral intermediates obtained during the above mentioned sequence of reactions were prone to racemization.

In another prior art process involving the intramolecular cyclization of thiazolidine required Collins oxidation as one of the steps. Use of heavy metals on an industrial scale would lead to problems during waste disposal. Moreover Wittig reaction on the aldehyde leads to a mixture of isomers, which should be separated and the desired isomer subjected to further reactions leading to biotin.

All these processes are however characterized by large number of synthetic steps resulting in low overall yields. The non-crystallizable intermediate stages mostly due to sugar nature are often obtained in impure form and require tedious purification on account of their polyfunctionality and chemical liability connected with it maintenance of comparatively very narrow range of reaction parameters. Additionally these sugars are not easily available in nature which leads to high prices.

In yet another process by Chavan, S. P.; Chittiboyina, A. G.; Kamat, S. K.; Kalkote, U. R.; and Ravindranathan, T. Indian Patents NF 211/00-A, NF 211/00-C describes the formation of 6-Benzyl-7-(1-trimethylsilyloxy-2-oxocyclohexyl)-3-phenyl-(3S, 7R, 7R)-perhydro-imidazo[1,5-C][1,3]thiazole-5-one.

OBJECTS OF THE INVENTION

The object of the present invention is to provide a process for the preparation of 5-methoxy-4-(methylthioalkyl)-1,3-bis(phenylmethyl)-2-imidazolindone having general formula (2a–d), avoiding the use of diisobutylaluminium hydride.

It is another object of the invention to provide a process for the preparation of 5-methoxy-4-(methylthioalkyl)-1,3-bis(phenylmethyl)-2-imidazolidone having general formula (2a–d) which has a good yield.

It is another object of the invention to provide a process for the preparation of 5-methoxy-4-(methylthioalkyl)-1,3-bis(phenylmethyl)-2-imidazolidone having general formula (2-a–d) which does not require substantial subsequent purification after formation, thereby lessening the cost of manufacture.

SUMMARY OF THE INVENTION

Accordingly, the present invention relates to a process for the preparation of 5-methoxy-4-(methylthioalkyl)-1,3-bis (phenylmethyl)-2-imidazolidone having general formula (2a–d)

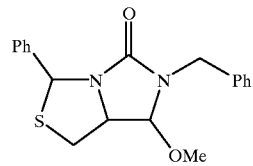

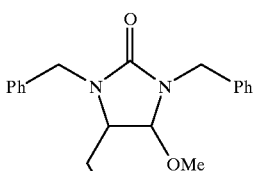

a: R = CH$_2$COCH$_2$CH$_2$CH$_2$COOMe
b: R = CH$_2$CH(OMe)$_2$
c: R = CH$_2$COOMe
d: R = H

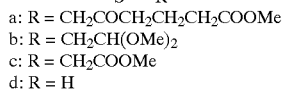

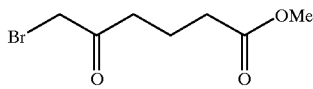

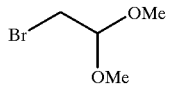

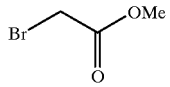

[wherein R=—CH$_2$COCH$_2$CH$_2$CH$_2$COOMe (2a), —CH$_2$CH(OMe)$_2$(2b); —CH$_2$COOMe(2c); —H (2d)] which comprises reacting a reducing agent with 6-benzyl-7-methoxy-3-phenylperhydroimidazo [1,5-c][1.3]thiozol-5-one of general formula (1) in the presence of an organic solvent for a period ranging from 0.5 to 2 hrs at a temperature ranging from −78° C. to 80° C., evaporating the solvent and reacting the residue with an alkylating reagent, optionally in the presence of a phase transfer catalyst and an inorganic base in an organic solvent for a period ranging from 10–12 hrs at room temperature, evaporating the solvent followed by purification to obtain the desired compound of general formula (2a–d).

In one embodiment of the invention, wherein the reducing agent used is a metal or a metal hydride selected from the group consisting of sodium, lithium, tributyltin hydride, potassium in ammonia or ethylenediamine and alkali metal in etheral or hydrocarbon solvent in the present of arene selected from the group consisting of naphthalene, biphenyl and 4,4'-ditertiary butyl alcohol.

In one embodiment of the invention, the organic solvent used is selected from the group consisting of benzene, toluene, acetone, THF and dioxane.

In another embodiment of the invention, the phase transfer catalyst used in selected from tetrabutylammonium hydrogensulphate and tetrabutylammonium bromide.

In another embodiment of the invention, the inorganic base is selected from the group consisting of potassium carbonate, sodium carbonate, sodium hydroxide and potassium hydroxide.

In another embodiment of the invention, the alkylating agent used is selected from the group consisting of methylchloroacetate, ethylbromoacetate and methyl-6-bromo-5-oxo-hexanoate.

In another embodiment of the invention, the compound 6-benzyl-7-methoxy-3-phenylperhydroimidazo[1,5-c][1.3]thiozol-5-one having general formula (1), can be prepared by reported procedure (Chimia, 41, 148–150 (1987)) from L-cysteine.

DETAILED DESCRIPTION OF THE INVENTION

The process of the present invention described herein below with reference to examples which are illustrative only and should not be construed to limit the scope of the present invention in any manner.

EXAMPLE 1

To 0.340 parts (1 mmol part) of compound 6-benzyl-7-methoxy-3-phenylperhydroimidazo[1,5-c] [1.3]thiozol-5-one of having formula (1) in anhydrous benzene (10 parts) was added azobisisobutyronitrile (0.164 parts; 1 mmol parts) and tributyl tin hydride (0.363 parts; 1.25 mmole parts) and the reaction mixture was refluxed for 30 minutes. The reaction was monitored by TLC. After completion of the reaction, organic solvent was evaporated and residue was stirred, with methyl-6-bromo-5-oxo-hexanoate (3a, 0.278 parts; 1.25 mmol parts) and anhydrous potassium carbonate (0.414 parts; 3 mmol parts) in anhydrous acetone for 12 hrs at room temperature. After filtration and evaporation of organic solvent, the residue was column chromatographed on silica gel using ethylacetate:pet.ether (35:65) as eluent to furnish compound methyl 6-(1,3-dibenzyl-5-methoxy-2-oxottetrahydro-1H-4-imidazolylmethylsulfanyl)-5-oxohexanoate of having formula (2a) in (0.290 parts; 0.6 mmole parts) 60% yield. $[\alpha]_D=+49.9°$ (c=1.26, $CHCl_3$).

EXAMPLE 2

To 0.340 parts (1 mmol part) of compound 6-benzyl-7-methoxy-3-phenylperhydroimidazo[1,5-c][1.3]thiozol-5-one of formula (1) in anhydrous benzene (10 parts) was added azobisisobutyronitrile (0.164 parts; 1 mmol parts) and tributyl tin hydride (363 parts; 1.25 mmole parts) and the reaction mixture was refluxed for 30 minutes. The reaction was monitored by TLC. After completion of the reaction, organic solvent was evaporated and residue was stirred, with bromo acetaldehydedimethyl acetal (3b 0.211 parts, 1.25 mmol parts) in benzene in the presence of tetrabutylammonium hydrogen sulphate and aqueous potassium hydroxide (20% 10 parts) for 8 hrs at room temperature. The organic layer was separated and on concentration and column purification on silica gel with ethyl acetate:pet.ether (25:75) as eluent provided compound 1,3-dibenzyl-4-(2,2-dimethoxyethylsulpanylmethyl)-5-methoxytetrahydro-1H-2-imidazolone of having formula (2b) (liquid, 0.215 parts; 0.5 mmol parts) in 50% yield. $^1H$ NMR=2.55 (d, 2H), 2.80 (dd, 1H), 3.08 (s, 3H), 3.28 (s, 3H), 3.30 (s, 3H), 3.40 (m, 2H), 4.12 (d, 2H), 4.35 (t, 1H), 4.50 (s,1H), 4.97 (dd, 2H), 7.58 (m, 10H) $[\alpha]_D=+53.6°$ (c=1.04, $CHCl_3$).

EXAMPLE 3

To 0.340 parts (1 mmol part) of compound (6-benzyl-7-methoxy-3-phenylperhydroimidazo[1,5-c][1.3]thiozol-5-one of having formula (1) in anhydrous toluene (10 parts) was added azobisisobutyronitrile (0.164 parts; 1 mmol parts) and tributyl tin hydride (0.363 parts; 1.25 mmole parts) and the reaction mixture was heated to 80° C. for 30 minutes. The reaction was monitored by TLC. After completion of the reaction methylchloroacetate (3c, 0.136 parts; 1.25 mmol parts) and anhydrous potassium carbonate (0.414 parts; 3 mmol parts) were added and stirred for 12 hrs at room temperature. After filtration and evaporation of organic solvent, the residue was column chromatorgraphed on silica gel using ethylacetate:pet.ether (25:75) as eluent to furnish compound methyl 2-(1,3-dibenzyl-5-methoxy-2-oxotetrahydro-1H-4-imidazolylmethyulsulfanyl)acetate of having formula 2c in (0.215 parts; 0.5 mmole parts) 60% yield. $^1H$ NMR=2.50 (m, 1H), 2.78 (dd, 1H), 3.03 (s, 3H), 3.40 (m, 1H), 3.68 (s, 3H), 4.12 (d, 2H), 4.50 (s, 1H), 4.95 (dd, 2H), 7.58 (m, 10H). $[\alpha]_D=+51.7$ (c=1.012, $CHCl_3$). $[\alpha]_D=+50.1°$ (c=1.264, $CHCl_3$).

EXAMPLE 4

To cooled (−78° C.) suspension of lithium (0.0347 parts) and naphthalene (0.0034 parts; 0.026 mmol parts) in tetrahydrofuran (5 parts) was added compound 6-benzyl-7-methoxy-3-phenylperhydroimidazo[1,5-c][1.3]thiozol-5-one of having formula (1) (0.340 parts; 1 mmole parts) in tetrahydrofuran (5 parts) and stirred for 3 hrs. The reaction was quenched with electrophile (water, 0.05 parts, 3 mmol parts) and temperature of the reaction was raised to 20° C. during 1 hr. The reaction mixture was filtered through celite and extracted with ethylacetate. One vaporating the organic solvent the residue 1,3-benzyl-4-methoxy-5-sulfanylmethyltetrahydro-1H-2-imidazolone of having formula (2d) was used as is for the next step i.e. alkylation as mentioned in example 1–3.

EXAMPLE 5

To cooled (−78° C.) suspension of lithium (0.0347 parts) and naphthalene (0.0034 parts; 0.026 mmol parts) in tetrahydrofuran (5 parts) was added compound 6-benzyl-7-methoxy-3-phenylperhydroimidazo[1,5-c][1.3]thiozol-5-one of having formula (1) (0.340 parts; 1 mmole parts) in tetrahydrofuran (5 parts) and stirred for 3 hrs. The reaction was quenched with electrophile (water, 0.05 parts, 3 mmol parts) and temperature of the reaction was raised to 20° C. during 1 hr. The reaction mixture was filtered through celite and extracted with ethylacetate. On evaporating the organic solvent the residue 1,3-benzyl-4-methoxy-5-sulfanylmethyltetrahydro-1H-2-imidazolone of having formula (2d) (0.342 parts, 1 mmole parts) was taken in benzene (10 parts) and 20% aqueous potassium hydroxide (10 parts) was added tetrabutyl ammonium hydrogen sulphate (0.001 mmole parts) and bromoacetaldehyde dimethylacetal (3b, 0.211 parts; 1.25 mmole parts) and stirred the reaction mixture for 6 hrs at room temperature. Then organic layer was separated. Concentration ad column purification on silica gel with ethyl acetate:pet.ether (25:75) as eluent provided compound 1,3-dibenzyl-4-(2,2-dimethoxyethylsulpanylmethyl)-5-methoxytetrahydro-1H-2-imidazolone of having formula (2b) (liquid, 0.215 parts; 0.5 mmole parts) in 50% yield.

EXAMPLE 6

To cooled (−78° C.) suspension of sodium (0.0347 parts) and naphthalene (0.0034 parts; 0.026 mmol parts) in tetrahydrofuran (5 parts) was added compound 6-benzyl-7-methoxy-3-phenylperhydroimidazo[1,5-c][1.3]thiozol-5-one of having formula (1) (0.340 parts; 1 mmole parts) in tetrahydrofuran (5 parts) and stirred for 3 hrs. The reaction was quenched with electrophile (water, 0.05 parts, 3 mmol parts) and temperature of the reaction was raised to 20° C. during 1 hr. The reaction mixture was filtered through celite and extracted with ethylacetate. On evaporating the organic solvent the residue (0.342 parts; 1 mmole parts) was taken in toluene (10 parts) and 20% aqueous potassium hydroxide (10 parts) was added tetrabutyl ammonium hydrogen sulphate (0.001 mmole parts) and bromoacetaldehyde dimethylacetal (3b, 0.211 parts; 1.25 mmole parts) and stirred the reaction mixture for 6 hrs at room temperature. Then organic layer was separated. Concentration and column purification on silica gel with ethyl acetate:pet.ether (25:75) as eluent provided compound 1,3-dibenzyl-4-(2,2-dimethoxyethylsulpanylmethyl)-5-methoxytetrahydro-1H-2-imidazolone of formula (2b) (liquid, 0.172 parts; 0.40 mmole parts) in 40% yield.

Advantages of the Process

Our process eliminates the use of diisobutylaluminium hydride (DIBAL-H) which is hazardous.

We claim:

1. A process for the preparation of 5-methoxy-4-(methylthioalkyl)-1,3-bis(phenylmethyl)-2-imidazolidone having general formula (2a–d)

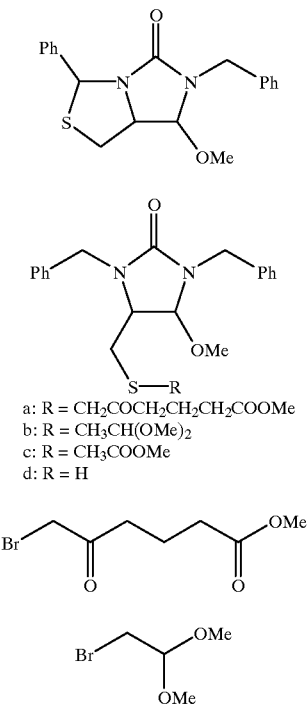

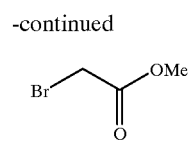

wherein R is —CH$_2$COCH$_2$CH$_2$CH$_2$COOMe (2a); —CH$_2$CH(OMe)$_2$(2b); —CH$_2$COOMe(2C); or —H(2d) which comprises reacting a reducing agent with 6-benzyl-7-methoxy-3-phenylperhydromimidazo[1,5-c][1.3]thiozol-5-one of general formula (1) in the presence of an organic solvent for a period ranging from 0.5 to 2 hrs at a temperature ranging from −78° C. to 80° C., evaporating the solvent and reacting the residue with an alkylating reagent, optionally inthe presence of a phase transfer catalyst and an inorganic base in an organic solvent for a period ranging from 10–12 hrs at room temperature, evaporating the solvent followed by purification to obtain the desired compound of general formula (2 a–d).

2. A process as claimed in claim 1 wherein the reducing agent used is a metal or a metal hydride selected from the group consisting of sodium, lithium, tributyltin hydride, potassium in ammonia or ethylenediamine and alkali metal in etheral or hydrocarbon solvent in the presence of arene selected from the group consisting of naphthalene, and biphenyl.

3. A process as claimed in claim 2 wherein the organic solvent used is selected from the group consisting of benzene, toluene, acetone, THF and dioxane.

4. A process as claimed in claim 1 wherein the phase transfer catalyst used is selected from tetrabutylammonium hydrogensulphate and tetrabutylammonium bromide.

5. A process as claimed in claim 1 wherein the inorganic base used is selected from the group consisting of potassium carbonate, sodium carbonate, sodium hydroxide and potassium hydroxide.

6. A process as claimed in claim 1 wherein the alkylating reagent used is selected from the group consisting of methylchloracetate, ethylbromoacetate and methyl-6-bromo-5-oxo-hexanoate.

* * * * *